US00PP16710P2

(12) United States Plant Patent
Stemkens

(10) Patent No.: US PP16,710 P2
(45) Date of Patent: Jun. 27, 2006

(54) ***VERBENA* PLANT NAMED 'AMARENA'**

(50) Latin Name: *Verbena hybrid*
Varietal Denomination: Amarena

(75) Inventor: Henricus G. W. Stemkens, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 240 days.

(21) Appl. No.: 11/003,501

(22) Filed: Dec. 3, 2004

(51) Int. Cl.
*A01H 5/00* (2006.01)

(52) U.S. Cl. ..... Plt./308
(58) Field of Classification Search ..... Plt./308
See application file for complete search history.

*Primary Examiner*—Anne Marie Grunberg
(74) *Attorney, Agent, or Firm*—Edouard G. Lebel

(57) ABSTRACT

A new and distinct variety of *Verbena* plant particularly distinguished by its deep red flower, early flowering and a habit that is first semi-erect and later spreading.

1 Drawing Sheet

Latin name of the genus and species of the plant claimed: *Verbena* hybrid.
Varietal denomination: 'Amarena'.

BACKGROUND OF THE NEW PLANT

The present invention comprises a new distinct cultivar of *Verbena*, botanically known as *Verbena×hybrida*.

The new cultivar is propagated from cuttings resulting from the cross of 'B742' and 'B728'. 'B742' is a scarlet flowering *Verbena* having a spreading habit. 'B742' is not commercially available and is not known by any synonyms. 'B728' is a deep rose flowering *Verbena* having a semi-erect habit. 'B728' is not commercially available and is not known by any synonyms. Neither 'B742' or 'B728' has been patented.

As a result of this cross the present cultivar was created in 2000 in Enkhuizen, Netherlands and has been repeatedly asexually reproduced by cuttings in Enkhuizen, Netherlands and Sarrians, France over a three year period. It has been found to retain its distinctive characteristics through successive propagations, and this novelty appears to be firmly fixed.

This new *Verbena* plant is an annual in most climatical zones in the US, only in zones 9 and 10 it is a perennial plant.

DESCRIPTION OF THE DRAWING

This new *Verbena* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Verbena*. The data that define these characteristics were collected from asexual reproductions carried out in Enkhuizen, Netherlands. The plant history was taken on 14 weeks old plants, blossomed under natural light in a greenhouse and grown in a 10.5 cm container. Colour readings were taken in the greenhouse under ambient light. Colour references are primarily to The R.H.S. Colour Chart of The Royal Horticultural Society of London.

TABLE 1

Differences between the new cultivar 'Amarena', its parents and a similar cultivar

| | 'Amarena' | 'B742' | 'B728' | 'Charmena' |
|---|---|---|---|---|
| Flower color | Deep red | Scarlet | Deep rose | Cherry red |
| Earliness | Early | Very early | Late | Very early |
| Seed set | No | No | Much | No |
| Mildew resistance | Good | No | Good | No |

The commercial name of the most resembling variety is 'Babylon cherry red'. The patented name of this variety is 'Charmena' and its U.S. Plant Pat. No. is 11,134.

The plant:

*Classification.*—Botanical: *Verbena×hybrida.*

*Parentage.*—Female parent: A seedling named 'B742' is one of our seedlings from our B-generation of plants bred in 1998. Pollen parent: A seedling named 'B728' is one of our seedlings from our B-generation of plants bred in 1998.

*Growth habit.*—Semi-erect later spreading, decumbent.

*Plant height.*—14–20 cm.

*Spreading area of plant.*—35–60 cm.

*Strength.*—Resistant to hot (30° C.–40° C.) and cold (0° C. –10° C.) weather.

*Branching character.*—Freely branching and lateral branching at every node.

*Blooming period.*—From April until November.

The stem:

*Diameter.*—2–2.5 mm.

*Length.*—15–25 cm.

*Shape.*—Tetragonal.

*Anthocyanin pigmentation.*—Absent.

*Color of the stem.*—141B.

*Length of internode.*—15–30 mm, depending on the light where the plant is propagated.

*Pubescence.*—Slightly pubescent.

*Length lateral branches.*—15–25 cm.

The foliage:

*Phyllotaxis.*—Opposite.

*Shape of blade.*—Ovate.

*Texture.*—*Upper side: Smooth. Lower side: Smooth.*

*Venation.*—Pinnate.
*Leaf margin.*—Incised.
*Leaf base.*—Obtuse.
*Leaf apex.*—Acute to acuminate.
*Length.*—20–38 mm.
*Width.*—18–26 mm.
*Depth of incision.*—6–10 mm.
*Number of incisions.*—2–5 per leaf.
*Color.*—Upper side: 137A (bit darker). Lower side: 137B.
*Pubescence.*—Some pubescence is present.
*Length of leaf stem.*—4–8 mm.
*Petiole surface structure.*—Slightly pubescent.
*Petiole diameter.*—2–4 mm.
*Petiole coloration.*—137A.

The bud:
*Peduncle length.*—15–30 mm, depending on season.
*Peduncle diameter.*—2–3 mm.
*Peduncle color.*—141B.
*Bud size.*—Diameter: 3 mm. Length: 8–12 mm.
*Bud shape.*—Elongated and ovate.
*Bud color.*—137D.
*Sepals.*—Color (upper side): 137B. Color (lower side): 137B. Form: Upright. Number: 5, fused. Length: 9–11 mm. Width: 3 mm. Shape: Elongated. Apex: Emarginate. Base: Fused. Margin: Entire.

The flower:
*Flower diameter.*—16–22 mm.
*Flower height.*—16–22 mm.
*Flower tube length.*—14–20 mm.
*Flower throat diameter.*—2–3 mm.
*Inflorescence.*—Corymb.
*Flower-form.*—Single, salverform; sessile on terminal corymbs.
*Petal color.*—Upper side: 53B, a bit more red. Lower side: 53D on the edge to N155A in the middle.
*Eye.*—A very small (1 mm) greenish Eye (155B) is present. Typically three out of the five petals exhibit this greenish coloration on the upper side of them.
*Overlapping of petals.*—Separate.
*No. of petals.*—Gamopetalous, 5 lobed.
*Petal apex.*—Obcordate.
*Petal base.*—Fused.
*Petal margin.*—Entire.
*Petal surface texture.*—Smooth.
*Size of the petal.*—Length: 6–8 mm. Width: 5–7 mm.
*Inflorescence.*—Length 25–30 mm. Diameter: 30–50 mm.
*Calyx length.*—12–16 mm.
*Calyx diameter.*—2–3 mm.
*Anthocyanin pigmentation of calyx limb.*—Absent.
*Color of the calyx.*—155C.
*No. of flowers per inflorescence.*—20–30.
*Fragrance.*—No fragrance.
*Bloom time of one inflorescence.*—New florets continue to open in one corymb over a period of 12 days.
*Lastingness of one flower.*—2 to 4 days.

Reproductive organs:
*Androecium.*—Stamens quantity: 4. Anther shape: Ovoid. Anther length: 1 mm. Anther color: 144B. Pollen amount: No pollen.
*Gynoecium.*—Pistils quantity: 1. Pistil length: 1.8–2.2 cm. Stigma shape: Bi-lobed. Stigma color: 144C. Style length: 1.6 cm. Style color: 144D. Ovary color: 144C.

No seedset is observed.

Roots:
*Type of roots.*—Fibrous. Roots start to grow on every part of the stem that contacts the soil, so not only at the nodes.

Physiological and ecological characteristics: Good tolerance to heat and cold.

Disease/pest resistance: Plants of the new *Verbena* have been observed to have strong resistance to diseases and pests, particularly to Powdery Mildew.

What is claimed is:

1. A new and distinct variety of *Verbena* plant named 'Amarena', substantially as illustrated and described herein.

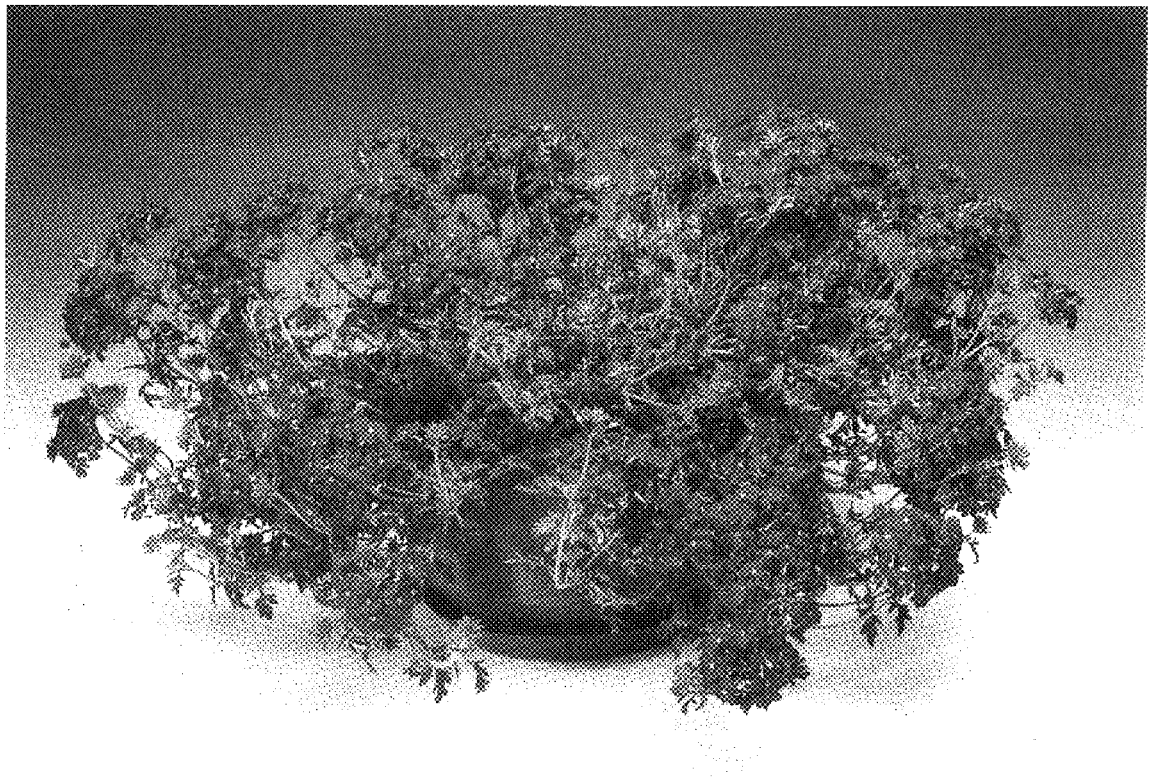

* * * * *